(12) United States Patent
Taufig

(10) Patent No.: US 6,902,559 B2
(45) Date of Patent: Jun. 7, 2005

(54) LIPOSUCTION DEVICE

(76) Inventor: Ahmmed Ziah Taufig, Turiner Strasse 2, 50668 Koeln (DE)

( * ) Notice: Subject to any disclaimer, the term of this patent is extended or adjusted under 35 U.S.C. 154(b) by 0 days.

(21) Appl. No.: 10/296,627

(22) PCT Filed: May 30, 2001

(86) PCT No.: PCT/EP01/06142
§ 371 (c)(1),
(2), (4) Date: Nov. 26, 2002

(87) PCT Pub. No.: WO01/91827
PCT Pub. Date: Dec. 6, 2001

(65) Prior Publication Data
US 2003/0167053 A1 Sep. 4, 2003

(30) Foreign Application Priority Data
May 31, 2000 (DE) .................. 200 09 78605

(51) Int. Cl.⁷ .......................... A61M 1/00; A61B 17/20; A61B 17/32
(52) U.S. Cl. ..................... 604/542; 604/22; 604/35; 606/167
(58) Field of Search ............. 604/542, 39, 35–22, 604/523, 42, 264; 433/80; 601/162; 606/167

(56) References Cited

U.S. PATENT DOCUMENTS

| | | | |
|---|---|---|---|
| 5,135,482 A | * | 8/1992 | Neracher .................. 604/22 |
| 5,395,315 A | * | 3/1995 | Griep ...................... 604/35 |
| 5,766,194 A | * | 6/1998 | Smith ..................... 606/167 |
| 5,807,313 A | * | 9/1998 | Delk et al. ................ 604/35 |
| 5,968,008 A | * | 10/1999 | Grams ..................... 604/35 |
| 6,258,111 B1 | * | 7/2001 | Ross et al. ............... 606/171 |
| 6,503,263 B2 | * | 1/2003 | Adams ..................... 606/170 |

FOREIGN PATENT DOCUMENTS

| EP | 331313 A1 | * | 9/1989 | ......... A61H/23/02 |
|---|---|---|---|---|
| WO | WO 99/22656 | * | 10/1998 | ......... A61B/17/36 |

* cited by examiner

Primary Examiner—Nicholas D. Lucchesi
Assistant Examiner—Roz Maiorino
(74) Attorney, Agent, or Firm—Diller, Ramik & Wight

(57) ABSTRACT

The liposuction device (10) for removing subcutaneous fatty tissue (12) comprises a suction cannula (16) with suction openings (22) for sucking the subcutaneous fatty tissue (12) and an injection line (18) with an injection opening (20) for injecting a working fluid. The injection opening (20) is placed on the front end of the injection line (18) and is provided in the shape of a slit so that the working fluid exits in the shape of a fan (21). The width of the slit of the injection opening (20) is less than 1.0 mm. This constricts the injection opening so that the use of the working liquid is reduced to a justifiable quantity, at the same time, the exiting working fluid fan guarantees a uniform and effective removal of subcutaneous fatty tissue.

16 Claims, 2 Drawing Sheets

LIPOSUCTION DEVICE

BACKGROUND OF THE INVENTION

The invention relates to a liposuction device for removing subcutaneous fat.

For the operative removal of subcutaneous fat, liposuction devices are used which substantially consist of a suction cannula for sucking the subcutaneous fat. With its free end, the suction cannula is pierced through the skin so that subsequently, the fat below the skin can be sucked through a suction opening at the free end of the suction cannula. To be able to better suck the fat, a working fluid detaching the subcutaneous fat or the fatty tissue is injected into the subcutaneous fatty tissue by means of an injection device before the suction procedure. From U.S. Pat. No. 5,968,008, a liposuction device is known where the suction cannula and the injection line are combined in a single component. The injection opening for injecting the working fluid is located at the front end of the injection line. The injection opening is small and point-like and lies precisely in the longitudinal axis of the injection line. The working fluid jet exiting from the injection opening either consists of a bundled line-shaped liquid jet or of a water jet distributing extensively, but in an unpressurized manner, which fills a large volume space. Thus, the working fluid jet either causes a purely point-like tissue removal or else an extensive distribution of a weak working fluid funnel onto the subcutaneous fat or tissue.

SUMMARY OF THE INVENTION

It is the object of the invention to simplify the directed application of the working fluid onto subcutaneous fat parts.

According to the invention, the injection opening is disposed at the front injection line end and has a slit-like configuration so that a powerful working fluid fan exits. By means of the fan-shaped working fluid exit, a larger volume of subcutaneous fatty tissue can be loosened from or peeled off the skin in a directed but nevertheless uniform and speedy manner. Thereby, a uniform removal of subcutaneous fat is ensured and the formation of cavities or bulges by a non-uniform tissue removal is avoided. The width of the injection opening slit is smaller than 1.0 mm, particularly smaller than 0.1 mm. Depending on the width of the slit, the length of the slit amounts to one to several millimeter. Due to the small slit width, a relatively low working fluid consumption with a high removal power at the same time is ensured. On the one hand, the low working fluid consumption of less than 10 l/h has the advantage that the liposuction device has a lower working fluid consumption and can thus be configured correspondingly smaller. Further, the low working fluid consumption has the medically important advantage that also only a relatively small amount of the suction liquid is injected into the respective subcutaneous fat portion and has to be sucked again through the suction cannula. It is easier to check the suction of smaller amounts of the mixture of working fluid and fat so that an undesired inflation of subcutaneous fat portions due to working fluid is avoided.

Preferably, the injection line comprises a funnel-shaped acceleration nozzle at its injection opening-side end. Before the working fluid exits through the slit-shaped injection opening, it is accelerated to a high speed in the acceleration nozzle. Thus, the injection liquid is already accelerated to its exit speed shortly before it reaches the injection opening. Thereby, the formation of a precise working fluid fan is realized.

Preferably, the injection opening is arranged so as to be inclined to the longitudinal axis of the injection line at an angle between 3° and 45° so that the working fluid fan exits at this angle to the longitudinal axis of the injection line. This means that the working fluid fan is not parallel to the longitudinal axis of the injection line but angled thereto. By the angling, the working fluid jet fan can be directed to the subcutaneous fat lying under the skin surface without any problem. Thereby, the peeling of the subcutaneous fat off the skin is considerably simplified. Preferably, the slit-like injection opening is arranged so as to be inclined at an angle of 10° to 30°, particularly of approximately 18°, to the longitudinal axis of the injection line. As experiments have shown, it is particularly advantageous to angle the working fluid fan at an angle between 10° and 30° for an effective peeling and removal of subcutaneous fat.

According to a preferred embodiment of the invention, a working fluid pump for pumping the working fluid to the injection opening is provided, the delivery pressure of the working fluid pump being adjustable by a pressure selector. The pressure of the working fluid and thus the pressure of the exiting working fluid fan is thus able to be adapted to the respective situation. In this manner, it is possible to realize a speedy removal of large subcutaneous fat volumes as well as a cautious removal of thin subcutaneous fat layers. Thereby, the traumatizing of non-fatty tissue in particular is kept on a low level.

Preferably, a suction pump for sucking the subcutaneous fat and a control device controlling the suction power of the suction pump in dependence on the pump power of the working fluid pump are provided. In case of a high pump power, i.e., with large amounts of working fluid injected, the suction power, i.e. the amount of the mixture of working fluid and subcutaneous fat pumped out, is increased correspondingly. Thus, it is ensured that an inflation of the hypodermis by working fluid is avoided. At the same time, it is ensured that the detached subcutaneous fat including the injected working fluid is approximately completely and directly sucked so that the result of the subcutaneous fat removal is visible and can be judged immediately. In this manner, misjudgements of the question as to how much subcutaneous fat still has to be removed are avoided.

According to a preferred embodiment, a handle for holding the suction cannula and the injection line is provided, a pump switch for switching the working fluid pump being provided at the handle. Thus, the function of the working fluid pump can be controlled conveniently and directly. Thereby, the directed removal of particular subcutaneous fat parts is considerably simplified.

Preferably, an ultrasonic generator for loosening the tissue is arranged at the suction cannula. The ultrasonic generator is arranged near the injection opening, if possible, to produce, by means of the generated ultrasound, an as great loosening effect as possible in the target region of the injected working fluid.

Alternatively or additionally, a laser may also be provided at the suction cannula, for heating and detaching the tissue. By the laser-supported tissue heating, the detachment and removal of the subcutaneous fat is simplified.

According to a preferred embodiment, the injection line with the injection opening is axially movable with respect to the handle. Further, an axial drive is provided that drives the injection line with the injection opening in an axially oscillating manner. Thus, an axial oscillating movement of the working fluid fan is realized whereby a persistence of the working fluid fan and thus an undesired digging of the working fluid fan into the tissue is avoided. Thereby, the security against the working fluid fan penetrating too deep into the tissue is increased.

According to a preferred embodiment, the injection line is arranged centrally within the suction cannula. Thus, a compact construction of the liposuction device is realized. Alternatively or additionally, the injection line can also be mounted so as to be adjacent the suction cannula outside. It is also possible to arrange several injection lines around the suction cannula.

Preferably, the suction cannula comprises several circumferentially distributed suction openings. Thus, the jacket of the suction cannula is configured so as to be perforated over a definite length. Thereby, the mixture of fat and working fluid can be sucked fast and the suction function will even be guaranteed if a suction opening is clogged.

Preferably, the working fluid pump is an interval pump for pumping the working fluid intermittently. The interval pump pumps the working fluid from a working fluid tank through a flexible line to the injection line. From the injection opening of the injection line, the working fluid exits intermittently or pulsatingly. Thus, the subcutaneous fat can be easily dissolved in its structure and finally sucked.

Hereinafter, an embodiment of the invention is explained in detail with reference to the drawings.

DESCRIPTION OF THE PREFERRED EMBODIMENTS

Figure 1:
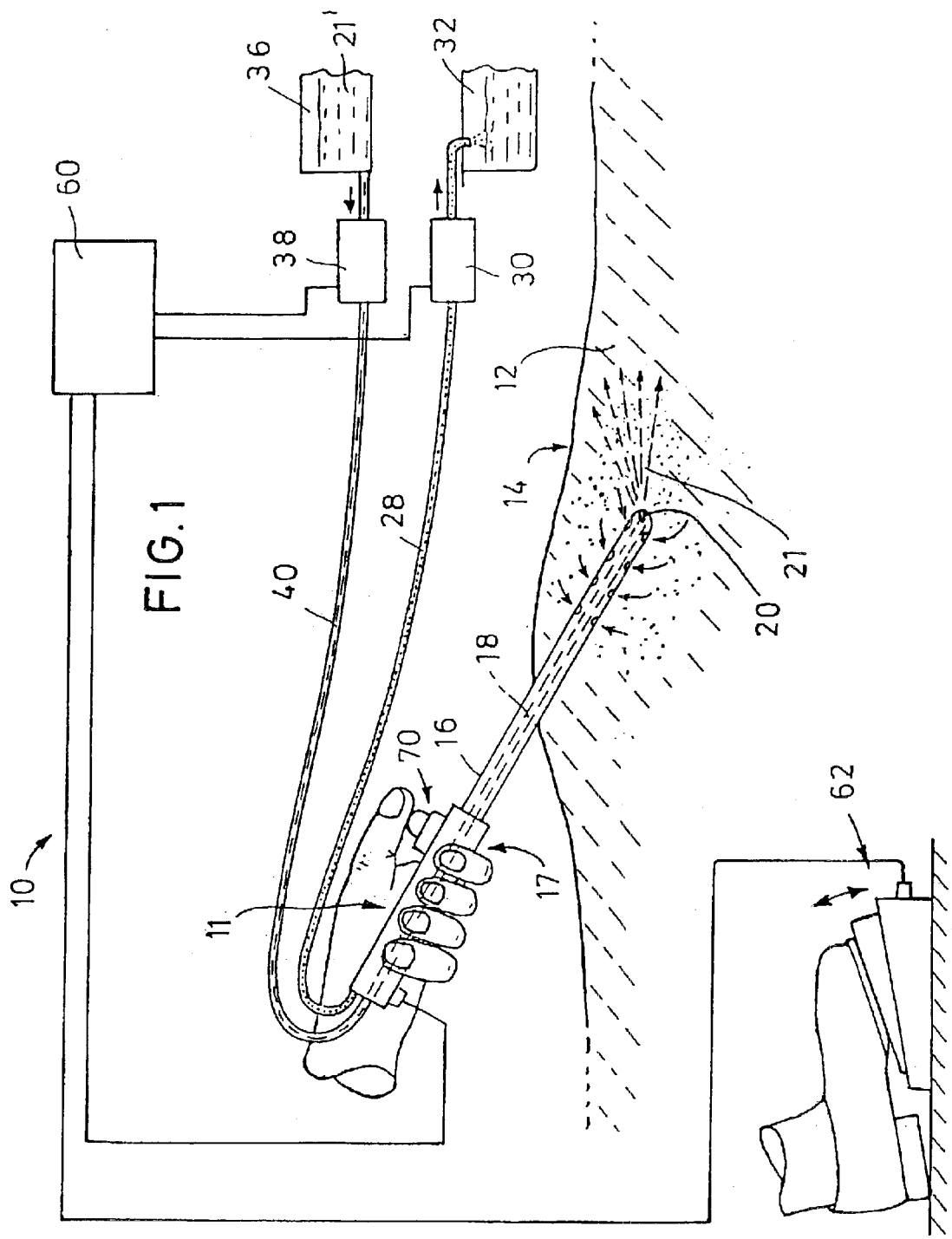
FIG. 1 shows a liposuction device according to the invention while sucking subcutaneous fat.

In FIG. 1, a liposuction device 10 for removing subcutaneous fat 12 below a skin surface 14 is illustrated. Substantially, the liposuction device 10 is formed by a suction lance 11, a working fluid tank 36, a waste tank 32, a control device 60, two pumps 38,30 with allocated liquid lines 28,40, a pressure selector 62 and a pump switch 70. The suction lance 11 is passed through a small cut opening in the skin 14 and dips, with its front end, into the subcutaneous fat 12 below the surface of the skin 14.

The liposuction lance 11 comprises a suction cannula 16 with a circular cross section, within which an injection line 18 is arranged axially and centrally in the middle. At its front end, the injection line 18 comprises a funnel-shaped acceleration nozzle 25 and a forwardly opened slit-shaped injection opening 20 through which a working fluid fan 21 is injected into the subcutaneous fat part 12. The injection opening 20 has a slit width of about 25 μm, but may also have a slit width of up to 100 μm and more. The length of the injection opening slit amounts to about 1.2 mm, but may also amount to several millimeter. The slit may have a straight or slightly bent configuration so that a plane working fluid fan 21 or a working fluid fan 21 curved in a funnel-like manner exits. In any case, the ratio of slit length to slit width is larger than 10. The fan angle β, i.e., the fan aperture angle, amounts to about 50 °.

At its free front end, the suction cannula 16 comprises several suction openings 22 at its circumference, through which the mixture of subcutaneous fat and working fluid is continuously sucked from the region below the skin surface 14 at a negative pressure of 0.5 to 0.9 bar. In its rear portion, the suction lance 11 comprises a handle 17 which is enlarged with respect to the front portion of the suction lance 11. In its front portion, the suction lance 11 has an outer diameter of about 4.0 mm. The free front end of the suction cannula 16 consists of stainless steel or of sapphire.

A working fluid pump 38 pumps the working fluid 21 from the working fluid tank 36 via a flexible line 40 into the injection line 18 of the suction lance 11. The pump 38 operates continuously, but can also be operated intermittently so that the working fluid is injected intermittently or pulsatingly. The working fluid is injected through the slit-shaped injection opening 20 at an overpressure of about 10–100 bar. Thereby, fatty tissue and fat are mechanically detached from the subcutaneous fat and disintegrated, but no vessels are destroyed. The consumption of working fluid with slit dimensions of 0.025 mm×1.2 mm amounts to about 5 l/h. The working fluid may contain pain-killing substances, but may also consist of mere salt solution.

Through a flexible line 28, the suction cannula 16 is connected with a suction pump 30 generating a negative pressure by which pump the sucked liquid is continuously pumped into a waste tank 32.

At the handle 17, a pump switch 70 is arranged that is connected with the control device 60 through a control line. By actuating the pump switch 70, the working fluid pump 38 and the suction pump 30 are switched on, upon release of the pump switch 70, both pumps 30, 38 are switched off again. Thus, a simple control of the operation of the liposuction device 10 is possible and it is possible at any time to switch it off quickly in order to avoid undesired removals.

The delivery pressure of the working fluid pump 38 is set by the pressure selector 62 configured as foot pedal and also connected to the control device 60 through a control line. By means of the foot pedal pressure selector 62, it is possible to adjust and adapt the delivery pressure and/or the flow rate of the working fluid pump 38 at any time according to the operator's discretion. Through the control device 60, the suction power of the suction pump 30 is always controlled in fixed dependence on the pump power of the working fluid pump 38 selected by the pressure selector 62. This means that in case of high pump power of the working fluid pump 38, the suction power of the suction pump 30 is set correspondingly high. Thereby, it is ensured that about as much of the mixture of working fluid and subcutaneous fat is sucked at any time as working fluid is simultaneously injected and subcutaneous fat is detached. Thereby, it is ensured that the respective skin part is not inflated by working fluid and that the result of the liposuction is immediately detectable. The negative pressure of the suction pump 30 can be limited to a maximum negative pressure so that a firm attachment of the suction cannula in the subcutaneous tissue is excluded.

The angle α of the injection opening 20 to the longitudinal axis of the injection line 18 and the suction lance 11, respectively, amounts to about 18°. The fan angle β, i.e., the aperture angle of the injection opening, amounts to about 50°. The suction cannula 16 as well as the injection line 18 each comprise a coupling member 75,76, so that the front ends of the suction cannula 16 and the injection line 18, which together form a lance tip 80, can be exchanged in a simple manner. Thus, the lance tip 80 can always be exchanged with simple means, for mounting an injection opening with another slit shape, another aperture angle, another setting angle α, etc., for example.

Although a preferred embodiment of the invention has been specifically illustrated and described herein, it is to be understood that minor variations may be made in the apparatus without departing from the spirit and scope of the invention, as defined by the appended claims.

Figure 2:
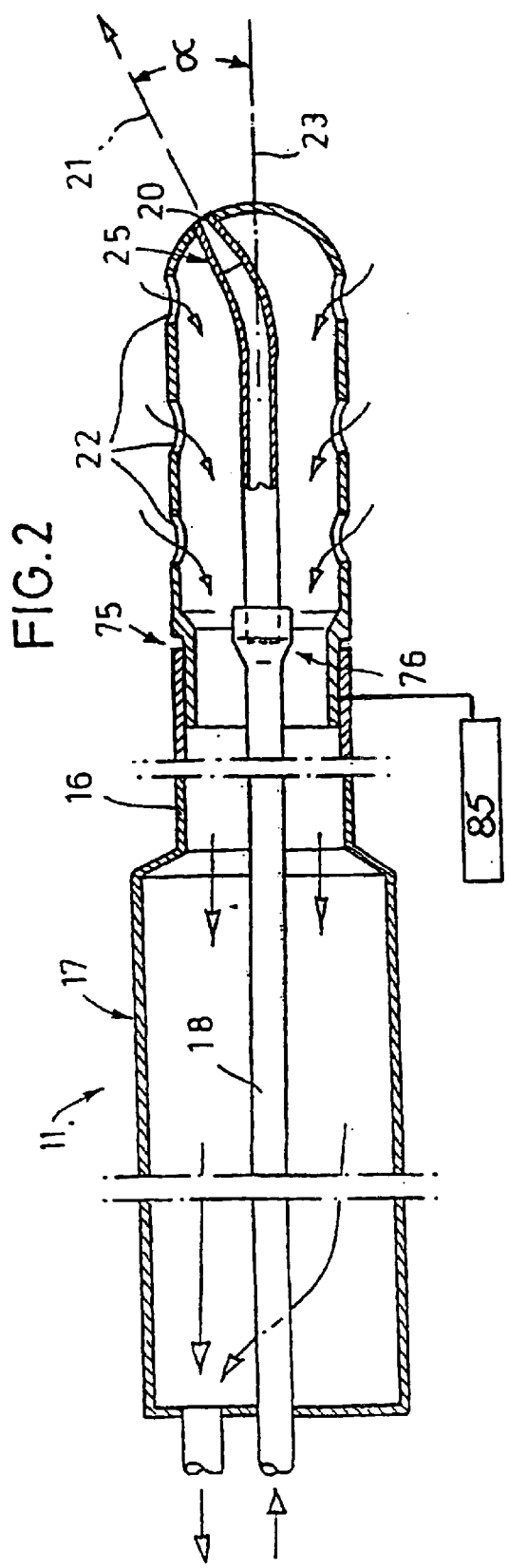
FIG. 2 shows a longitudinal section through the suction cannula of the liposuction device of FIG. 1.
Figure 3:
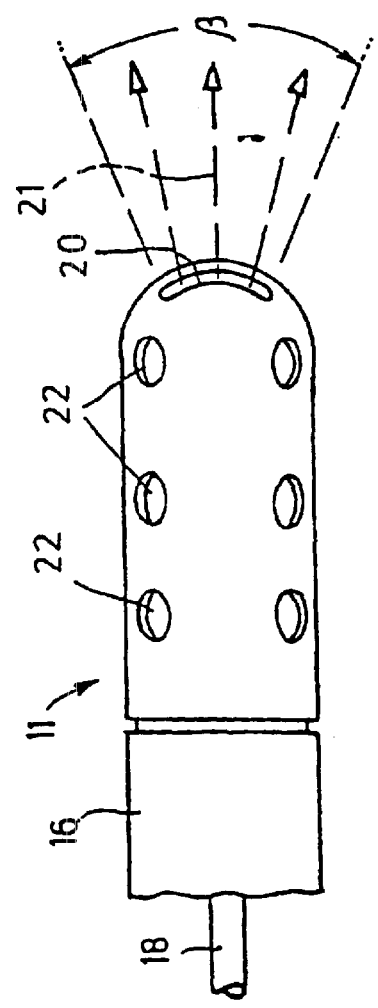
FIG. 3 shows the suction cannula of the liposuction device of FIG. 1.

The injection line 18 is preferably axially movable with respect to the handle 17. Preferably, an axial drive 85 (FIG. 2) is provided that drives the injection line 18 and the injection opening or openings 20 in an axially oscillating manner which imparts an axial oscillating movement to the working fluid fan 21 thus avoiding undesired digging of the working fluid fan 21 into the tissue below the skin surface 14.

What is claimed is:

1. A liposuction device for removing subcutaneous fat (12) comprising a cannula (16) having a suction opening (22) for sucking therethrough subcutaneous fat (12), an injection line (18) for delivering a working fluid to an injection opening (20) of the cannula (16), the injection opening (20) being constructed and arranged at a front end of the injection line (18) and having a slit-shaped configuration whereby the working fluid exits the injection opening (20) forwardly of the front end in the shape of a working fluid fan (21), the width of the slit-shaped injection opening (20) being smaller than 1.0 mm, the slit-shaped injection opening (20) being inclined to a longitudinal axis (23) of the injection line (18) at an angle ($\alpha$) thereto ranging substantially between 3 to 45° so that the working fluid fan (21) exits at said angle ($\alpha$) with respect to the longitudinal axis (23), and the slit-shaped injection opening (20) being the only opening located at the front end of the injection line.

2. The liposuction device as defined in claim 1 wherein the injection line (18) includes a funnel-shaped acceleration nozzle (25) with an end portion converging toward said slit-shaped injection opening (20).

3. The liposuction device as defined in claim 1 including a fluid pump (38) for pumping working fluid to the injection opening (20), and pressure selector means (62) for selectively adjusting the delivery pressure of the fluid pump (38).

4. The liposuction device as defined in claim 1 including a handle (17) for holding the cannula (16) and the injection line (18), a fluid pump (38) for pumping working fluid to the injection opening (20), and a pump switch (70) at the handle (17) for controlling the operation of the fluid pump (38).

5. The liposuction device as defined in claim 1 including a fluid pump (38) for pumping working fluid to the injection opening (20), and the working fluid pump (38) is an interval pump for intermittently pumping the working fluid (21).

6. The liposuction device as defined in claim 1 including a handle (17) at an end of the cannula (16) opposite the injection opening (20), and means (85) for axially oscillating the injection opening (20) relative to the handle (17).

7. The liposuction device as defined in claim 1 wherein the injection line (18) is arranged substantially centrally of the cannula (16), and the cannula (16) includes additional suction openings (22) distributed over a circumferential wall thereof.

8. The liposuction device as defined in claim 1 wherein the range of the angle ($\alpha$) is preferably substantially between 10 through 30°.

9. The liposuction device as defined in claim 1 wherein the angle ($\alpha$) is preferably substantially 18 degrees.

10. The liposuction device as defined in claim 1 wherein the slit width of the injection opening (20) is smaller than substantially 0.1 mm.

11. A liposuction device for removing subcutaneous fat (12) comprising a cannula (16) having a suction opening (22) for sucking therethrough subcutaneous fat (12), an injection line (18) for delivering a working fluid to an injection opening (20) of the cannula (16), the injection opening (20) being constructed and arranged at a front end of the injection line (18) and having a slit-shaped configuration whereby the working fluid exits the Injection opening (20) forwardly of the front end in the shape of a working fluid fan (21), the width of the slit-shaped injection opening (20) being smaller than 1.0 mm, the slit-shaped injection opening (20) being inclined to a longitudinal axis (23) of the injection line (18) at an angle ($\alpha$) thereto ranging substantially between 3 to 45° so that the working fluid fan (21) exits at said angle ($\alpha$) with respect to the longitudinal axis (23), the slit-shaped injection opening (20) being the only opening located at the front end of the injection line, a working fluid pump (38) for pumping working fluid to the injection opening (20), a suction pump (30) for sucking the subcutaneous fat (12), and control means (60) for controlling the suction power of the suction pump (30) in dependence on the pumping power of the working fluid pump (38).

12. The liposuction device as defined in claim 11 wherein the injection line (18) includes a funnel-shaped acceleration nozzle (25) with an end portion converging toward said slit-shaped injection opening (20).

13. The liposuction device as defined in claim 11 wherein the injection line (18) is arranged substantially centrally of the cannula (16), and the cannula (16) includes additional suction openings (22) distributed over a circumferential wall thereof.

14. A liposuction device for removing subcutaneous fat (12) comprising a cannula (16) having a suction opening (22) for sucking therethrough subcutaneous fat (12), an injection line (18) for delivering a working fluid to an injection opening (20) of the cannula (16), the injection opening (20) being constructed and arranged at a front end of the injection line (18) and having a slit-shaped configuration whereby the working fluid exits the injection opening (20) in the shape of a fan (21), a handle (17) at an end of the cannula (16) opposite the injection opening (20), and means (85) for axially oscillating the injection opening (20) relative to the handle (17).

15. The liposuction device as defined in claim 14 wherein the injection line (18) includes a funnel-shaped acceleration nozzle (25) with an end portion converging toward said slit-shaped injection opening (20).

16. The liposuction device as defined in claim 14 wherein the injection line (18) is arranged substantially centrally of the cannula (16), and the cannula (16) includes additional suction openings (22) distributed over a circumferential wall thereof.

* * * * *